United States Patent [19]

Hess

[11] 4,144,890
[45] Mar. 20, 1979

[54] CONTACT DEVICE FOR MUSCLE STIMULATION

[75] Inventor: Stanley R. Hess, Miami, Fla.

[73] Assignee: Cordis Corporation, Miami, Fla.

[21] Appl. No.: 751,386

[22] Filed: Dec. 19, 1976

Related U.S. Application Data

[60] Division of Ser. No. 688,238, May 20, 1976, Pat. No. 4,066,085, which is a continuation of Ser. No. 540,805, Jan. 14, 1975, abandoned.

[51] Int. Cl.² ............................................. A61N 1/04
[52] U.S. Cl. ................................ 128/418; 128/419 P
[58] Field of Search .................. 128/418, 419 P, 404, 128/2.06 E, 2.1 E, DIG. 4

[56] References Cited

U.S. PATENT DOCUMENTS

| 3,216,424 | 11/1965 | Chardack | 128/418 |
| 3,253,595 | 5/1966 | Murphy, Jr. et al. | 128/418 X |
| 3,750,650 | 8/1973 | Ruttgers | 128/2.06 E |
| 3,754,555 | 8/1973 | Schmitt | 128/418 |
| 3,814,104 | 6/1974 | Irnich et al. | 128/418 |
| 3,827,428 | 8/1974 | Hon et al. | 128/2.06 B |
| 3,835,864 | 9/1974 | Rasor et al. | 128/419 P |
| 3,880,169 | 4/1975 | Starr et al. | 128/418 |
| 3,902,501 | 9/1975 | Citron et al. | 128/418 |
| 3,973,555 | 10/1976 | Moller | 128/2.1 E |

FOREIGN PATENT DOCUMENTS

| 2053919 | 5/1972 | Fed. Rep. of Germany | 128/419 P |
| 6804714 | 10/1968 | Netherlands | 128/418 |

Primary Examiner—Lee S. Cohen
Attorney, Agent, or Firm—Kenway & Jenney

[57] ABSTRACT

The contact device disclosed herein is designed for applying stimulating pulses to cardiac muscle tissue to obtain artificial pacing of the heart. Fibrosis around the stimulating electrode itself is minimized by employing a non-binding, preferably quite flexible electrode to establish the contact and using relatively stiff, prong-like attaching members which are separate and substantially spaced from the stimulating electrode itself.

2 Claims, 7 Drawing Figures

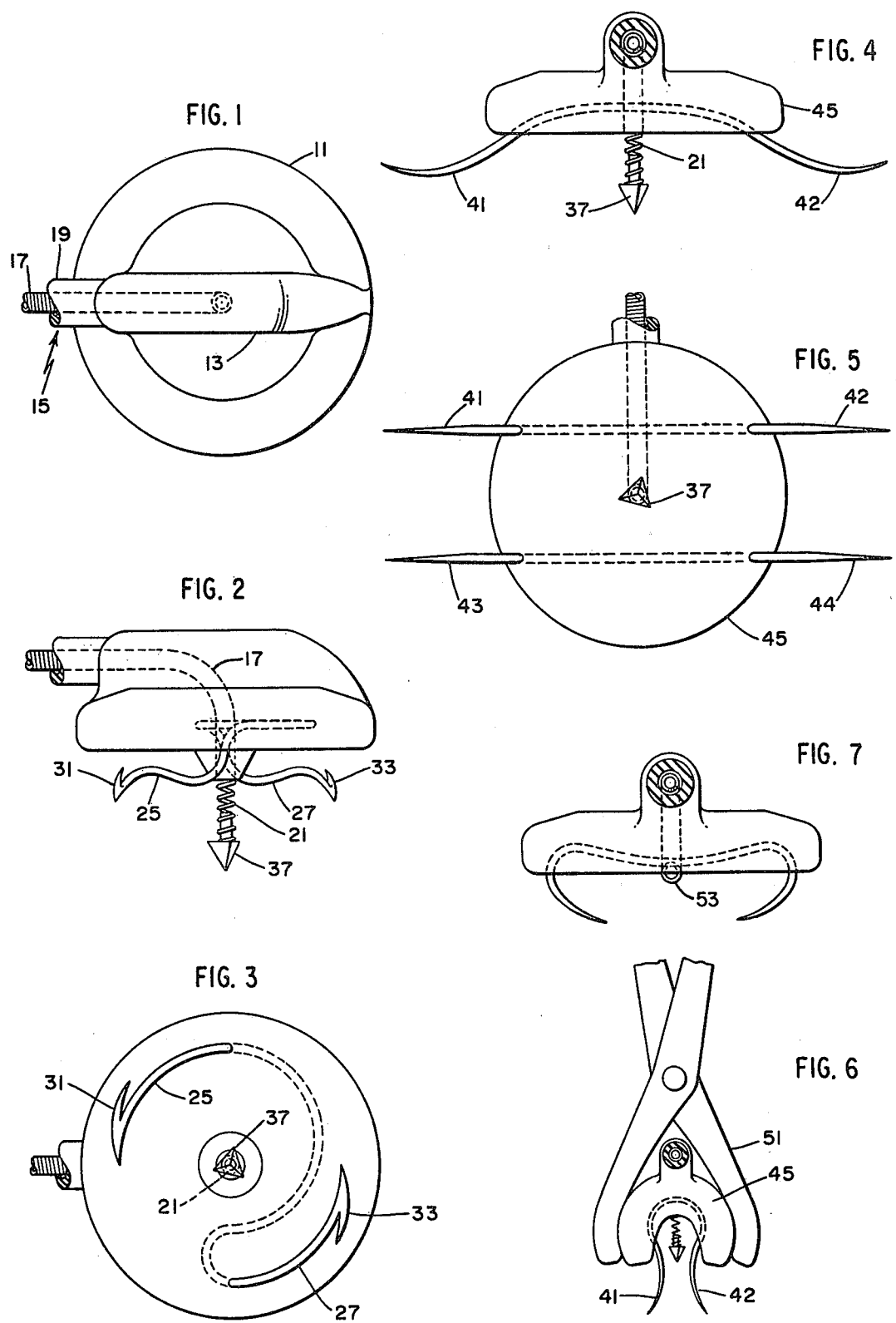

CONTACT DEVICE FOR MUSCLE STIMULATION

CROSS-REFERENCE TO RELATED APPLICATIONS

This application is a division of application Ser. No. 688,238, filed May 20, 1976, now U.S. Pat. No. 4,066,085, which is itself a continuation of application Ser. No. 540,805, filed Jan. 14, 1975, now abandoned.

BACKGROUND OF THE INVENTION

This invention relates to a contact device for muscle stimulation and in particular to an epicardial electrode used in connection with cardiac pacemakers.

In cardiac pacemaking systems, electrical impulses are delivered to the heart through electrodes which may be either internal or external of the heart. The former are inserted intravenously and contact the heart within the atrial or ventricular, chamber depending upon the type of stimulation desired. External leads are attached to the external heart muscle, generally by suturing the lead to the heart or by using a so-called self-attaching electrode lead fashioned as a corkscrew which may be screwed into the heart muscle. With electrodes attached by suturing, it has usually been necessary to perform a thorocotomy to expose the heart so that the electrode can be sutured to it. Electrodes that are of the self-attaching type do not necessarily require a thorocotomy, and in that sense are easier and safer to attach. They do, however, suffer from the development of fibrosis which has a tendency to interfere with the electrical contact and impair the efficiencies of the electrode. The present invention is aimed at providing an electrode that overcomes both drawbacks, that is to say one which may be attached externally of the heart without requiring a thorocotomy but which does not produce significant fibrosis at the electrode contact.

SUMMARY OF THE INVENTION

Briefly, a muscle stimulating contact device in accordance with the present invention is typically constructed around the generally flat base formed of an insulating material such as silicone rubber. A non-binding electrode, e.g. a flexible helical coil, projects from one face of the base member and is adapted to electrically contact the muscle to be stimulated, e.g. through a stab wound. A pair or more of relatively stiff, prong-like attaching members project from the base at locations substantially spaced from the flexible electrode. The prong-like attaching members retain the device in essentially fixed position independently of the non-binding electrode so that fibrosis is confined mainly to the environment of the attaching members and a desirable contact and stimulation threshold is maintained for a relatively long period.

BRIEF DESCRIPTION OF THE DRAWINGS

FIG. 1 is a plan view of a muscle stimulating contact device constructed in accordance with the present invention;

FIG. 2 is a side view of the contact device of FIG. 1;

FIG. 3 is a bottom view of the contact device of FIG. 1;

FIG. 4 is an end view of another embodiment of a contact device in accordance with the present invention;

FIG. 5 is a bottom view of the contact device of FIG. 4;

FIG. 6 is a view of the contact device of FIG. 4 being held by an inserting tool in a flexed position which facilitates application of the contact device to cardiac tissue; and, FIG. 7 is an end view of a still further embodiment.

Corresponding reference characters indicate corresponding parts throughout the several views of the drawings.

DESCRIPTION OF THE PREFERRED EMBODIMENTS

Referring now to FIGS. 1-3, there is illustrated a contact device which is adapted to be applied to external cardiac tissue with a twisting motion, i.e about ¼ turn. The contact device employs a generally flat base member 11 formed of an insulating material. Preferably, this material is relatively flexible, medical-grade silicone rubber being the preferred material. The base 11 is provided with an upstanding tab portion 13 which permits the base to be easily held in a pair of forceps for application.

Extending from the tab portion of the base 11 is a lead 15 which provides a means of connection to an electrical stimulating circuit, e.g. a cardiac pacemaker. As is understood, the pacemaker circuit itself is typically implanted in a more easily accessible area remote from the heart. Lead 15 is preferably of a construction proven to be useful in pacemaker situations, which construction involves a helically-coiled wire conductor 17 enclosed within a silicone rubber tube 19.

Within the tab portion of the base 11, the coiled conductor 17 turns downwardly as seen in FIG. 2 and extends from the bottom face of the base member 11 so as to form a projecting electrode 21 comprising a series of spaced helical turns of wire. This wire is of a non-reactive material such as Elgiloy. As will be understood, this electrode is relatively flexible or floppy and will tend not to resist the natural movements of the heart in any manner which would stimulate the formation of fibrotic tissue. In this sense, the electrode 21 is non-binding as the term is construed herein.

Circumferentially spaced from the electrode 21, are two relatively stiff attaching members 25 and 27 which are needle-or prong-like in character. Preferably, the attaching members 25 and 27 constitute the opposite ends of a single piece of relatively stiff wire stock, the central portion of which is imbedded in the insulating material of the base member 11, e.g. during the original casting of the base member. As may be seen in FIGS. 2 and 3, the members 25 and 27 are shaped so as to permit the contact device to be "screwed in" to the cardiac muscle tissue during the application of the device. The tips of the attaching members can be provided with fishhook-type barbs 31 and 33, respectively, to resist backing out of the attaching members 25 and 27.

While an electrode of the type indicated at 21 may be introduced into the cardiac tissue by means of a stab wound provided in advance, a preferred method of permitting the electrode to pierce the cardiac tissue is to provide a highly sharpened, multifaceted point, as indicated at 37. Thus, a surgeon may attach the device, held in a pair of forceps, by first pushing the tip 37 into the tissue and then twisting approximately a ¼ turn so that the attaching members 25 and 27 imbed and lock the device in essentially fixed position relative to the cardiac muscle tissue.

In that the attaching members 25 and 27 are separate and spaced from the electrode 21, the formation of fibrotic tissue around these members will not interfere with the stimulation threshold established by the electrode 21. Since the electrode 21 itself is constructed so as to be relatively flexible and so as not to resist the natural movements of the heart muscle, i.e. so as to be non-binding, fibrosis is minimized and the stimulation threshold initially established will remain relatively stable.

In the embodiment illustrated in FIGS. 4–6, four laterally-projecting attachment members are provided, designated 41–44, each pair being constituted by the opposite ends of a stiff, spring wire member, the central portion of which is imbedded in an insulating base member 45. The base member 45 is essentially similar to that indicated at 11 in FIG. 1. The attaching members 41–44 are again relatively stiff and are sharpened to provide needle- or prong-like elements suitable for digging into and fixedly engaging muscle tissue.

While relatively stiff as compared with the relatively flexible electrode element 21, the attaching elements 41–44 are sufficiently resilient and springy to allow the base 45 to be flexed or folded by a pair of forceps 51 as illustrated in FIG. 6. The contact member may then be applied to a patient's heart by pressing the prong-like members 41–44 against the selected site and then slowly releasing the forceps. As the attaching member unfolds or flexes, the prong or needle-like elements 41–44 will spring outwardly and pierce the tissue and form a locking engagement therewith. At the same time, the electrode 21 will pierce the tissue through a stab wound created by a cutting member 37. Again, since the electrode 21 is relatively flexible as compared with the attaching members 41–44, the formation of fibrotic tissue will be confined mainly to the attaching members rather than to the electrode itself.

As will be understood, an analogous construction to that illustrated in FIGS. 4–6 can be devised in which the attaching prongs extend inwardly and the base is folded back rather than forward as in the embodiment illustrated. This is illustrated in FIG. 7. Similarly, while the relatively flexible, helically-coiled electrode construction which is introduced into the tissue to be stimulated through a stab wound is preferred, it should be understood that other types of non-binding electrode figurations may also be used so long as they do not form points of stiff attachment with the muscle tissue. One type of electrode which may be used is formed by allowing half turns of the helically-coiled conductor to project through the bottom face of the insulating base as illustrated at 53 in FIG. 7. In some cases, a small flat disk electrode resting against the tissue to be stimulated may also be entirely sufficient.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A pacemaker lead for application to cardiac muscle from outside the heart to effect stimulation, comprising:
   a generally flat base of flexible electrical insulating material including one relatively flat face;
   a relatively flexible coil of conductive wire extending perpendicularly from said base through said relatively flat face at a location disposed substantially centrally with respect to said base and having an end projecting outwardly of said base;
   two pairs of arcuate, pointed hooks partially embedded in said base and protruding through the same relatively flat face of
   said base as said coil, said hooks being insulated from said coil, the hooks in each pair facing each other in opposed relationship so that, by bending back said base, the hooks may be drawn apart;
   a sharp tip provided at the end of said coil; and a flexible insulated electrical lead-in wire connected to said coil and secured to said base, the wire and the coil being connected within said base,
   said lead-in wire extending outwardly from said base to allow its connection to a source of current,
   whereby, with the hooks drawn back, said coil may be inserted in cardiac muscle to establish an electrical connection to a pacemaker unit and said hooks can be released to engage the cardiac tissue and serve to anchor said coil and base to the cardiac muscle, said coil riding in non-binding relationship to said muscle.

2. A pacemaker lead for application to cardiac muscle from outside the heart to effect stimulation, comprising:
   a generally flat base of flexible electrical insulating material including one relatively flat face;
   a relatively flexible coil of conductive wire extending perpendicularly from said base through said relatively flat face, at a location disposed substantially centrally with respect to said base and having an end projecting outwardly of said base;
   two pairs of arcuate, pointed hooks partially embedded in said base and protruding through the same relatively flat face of said base as said coil, said hooks being insulated from said coil,
   the hooks in each pair facing outwardly away from each other so that, by folding said base forwardly toward the projecting end of said coil, the hooks may be brought closer together;
   a sharp tip provided at the end of said coil;
   and a flexible insulated electrical lead-in wire connected to said coil and secured to said base, the wire and the coil being connected within said base,
   said lead-in wire extending outwardly from said base to allow its connection to a source of current,
   whereby, with the hooks folded forward, said coil may be inserted in cardiac muscle to establish an electrical connection to a pacemaker unit and said hooks can be released to engage the cardiac tissue and serve to anchor said coil and base to the cardiac muscle, said coil riding in non-binding relationship to said muscle.

* * * * *